United States Patent [19]

Eppstein et al.

[11] Patent Number: 4,962,091
[45] Date of Patent: Oct. 9, 1990

[54] CONTROLLED RELEASE OF MACROMOLECULAR POLYPEPTIDES

[75] Inventors: Deborah A. Eppstein, Palo Alto; Brian B. Schryver, Redwood City, both of Calif.

[73] Assignee: Syntex (U.S.A.) Inc., Palo Alto, Calif.

[21] Appl. No.: 866,625

[22] Filed: May 23, 1986

[51] Int. Cl.$^5$ .................... A61K 31/12; A61K 47/00
[52] U.S. Cl. ............................... 514/2; 514/21; 514/964; 424/78; 424/89; 424/92; 424/85.1; 424/85.2; 424/85.6; 424/85.8; 424/85.4
[58] Field of Search .............. 424/78, 89, 85, 46, 424/92, DIG. 7, 486; 514/773, 772, 774, 775-778, 782, 951, 3-20, 958, 213, 21, 12-19, 2, 964

[56] References Cited

U.S. PATENT DOCUMENTS

| | | | |
|---|---|---|---|
| 3,773,919 | 11/1973 | Boswell et al. | 424/486 |
| 3,976,071 | 8/1976 | Sadek | 128/260 |
| 4,225,581 | 9/1980 | Kreuter et al. | 424/89 X |
| 4,293,539 | 10/1981 | Ludwig | 424/489 |
| 4,419,340 | 12/1983 | Yolles | 424/426 |
| 4,512,972 | 4/1985 | Schmidt-Ruppin | 424/89 |
| 4,613,500 | 9/1986 | Suzuki et al. | 424/78 X |
| 4,637,931 | 1/1987 | Schmitz | 424/78 |
| 4,678,809 | 7/1987 | Phillips | 424/78 X |

FOREIGN PATENT DOCUMENTS 0052510 5/1982 European Pat. Off. .
0058481 8/1982 European Pat. Off. .

OTHER PUBLICATIONS

*Journal of Bioengineering*, vol. 1, pp. 25-52 (1986).
*Journal of Pharmaceutical Sciences*, vol. 73, pp. 1294-1297 (1984).
*American Journal of Obstetrics and Gynecology*, vol. 140, pp. 799-806 (1978).
*Contraception*, vol. 13, pp. 375-384 (1976).

Primary Examiner—Matthew A. Thexton
Assistant Examiner—Catherine S. Kilby
Attorney, Agent, or Firm—Lester E. Johnson; Tom M. Moran; Alan M. Krubiner

[57] ABSTRACT

An active agent delivery system for the controlled administration of macromolecular polypeptides which comprises a micro-suspension of water-soluble components in a polylactide matrix.

42 Claims, 1 Drawing Sheet

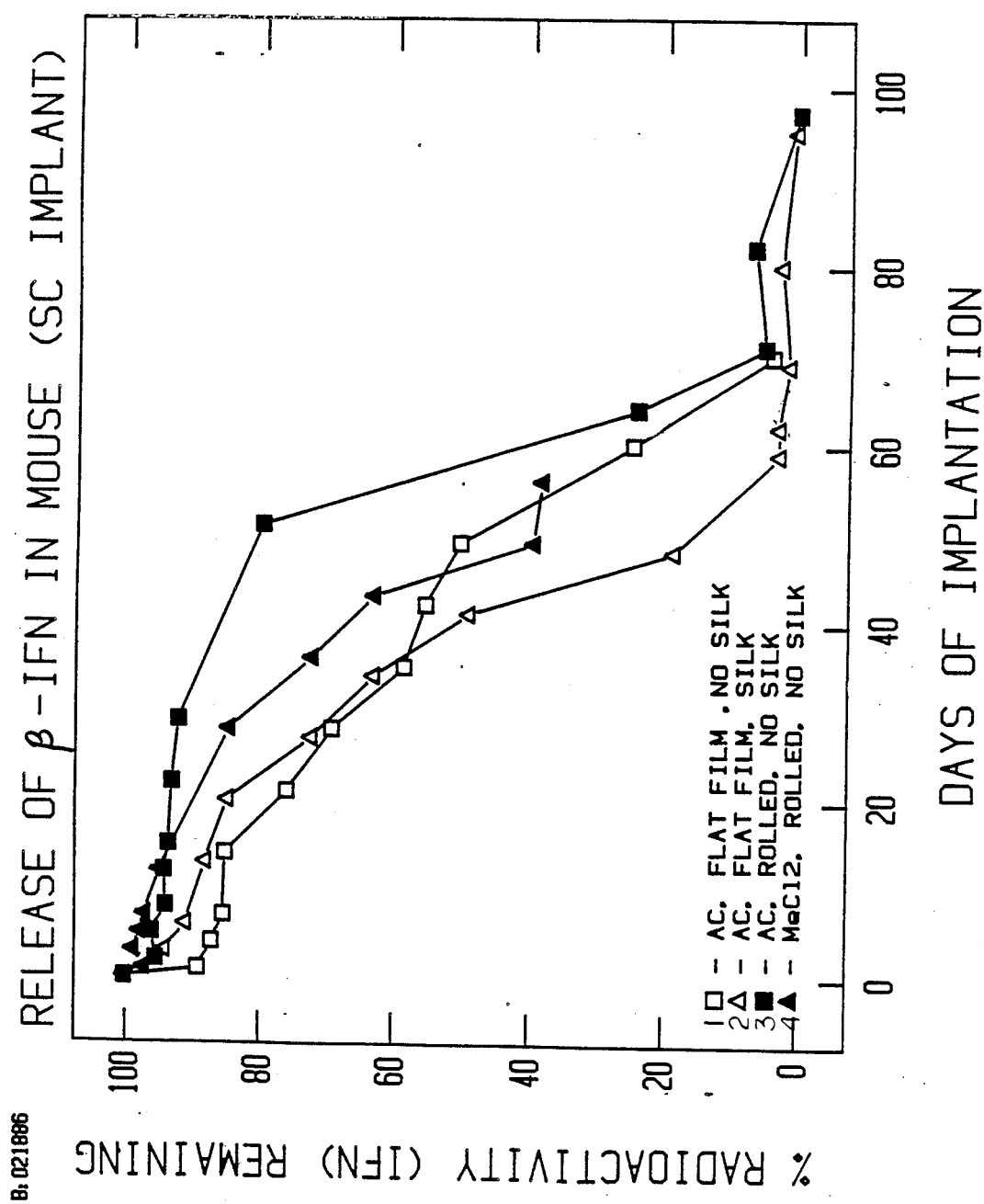

CONTROLLED RELEASE OF MACROMOLECULAR POLYPEPTIDES

BACKGROUND OF THE INVENTION

1. Field of the Invention:

This invention relates to an active agent delivery system for administering macromolecular polypeptide active agents having molecular weights of about 1000 or greater, particularly interferons, at a controlled rate for a prolonged period of time.

2. Background and Related Disclosures:

The traditional and most widely used method of administration of therapeutic agents is by the oral route. However, in the case of large polypeptides, such delivery is not feasible due to the hydrolysis of the peptides by digestive enzymes. The methods most commonly used for administration of polypeptide therapeutic agents are by repeated injection, intramuscular (IM), subcutaneous (SC) or intravenous (IV) infusion. These methods are acceptable in situations where a very limited number of injections are required, but are undesirable for chronic administration (for example as with insulin therapy). The nature of many of the diseases, disorders and conditions susceptible to improvement by polypeptide administration is chronic rather than acute, thus necessitating frequent injections over a prolonged period of time.

There is, therefore, a need for an efficacious and economical delivery system for large polypeptide agents. Biodegradable polymer matrices formed from polylactic acid or copolymers of polylactic acid with other comonomers such as polyglycolic acid have been used as sustained release delivery systems for a variety of active agents, due to their ability to biodegrade in situ. See, for example, U.S. Pat. Nos. 4,293,539, and 4,419,340. The use of these polymers in implants for delivery of several therapeutic agents has been disclosed in scientific publications and in the patent literature. See, for example, Anderson, L. C. et al, (1976), "An injectable sustained release fertility control system", *Contraception* 13: 375–384; Beck et al. (1979) "New long-acting injectable microcapsule contraceptive system", *Am. J. Obstet. Gynecol.* 140: 799–806; Yolles et al. (1978) "Timed release depot for anti-cancer agents II", *Acta Pharm. Svec.* 15: 382–388, U.S. Pat. No. 3,773,919, and U.S. patent application Ser. No. 699,715 filed Feb. 8, 1985. Sustained delivery of peptides from poly(lactide-co-glycolide) systems has been reported by Kent et al. (1982), "In vivo controlled release of an LHRH analog from injected polymeric microcapsules", *Contracept. Deliv. Syst.* 3: 58; by Sanders et al. (1984), "Controlled release of a luteinizing hormone-releasing hormone analogue from poly (d,l-lactide-co-glycolide)-microspheres", *J. Pharmaceut. Sci.* 73: 1294–1297, by T. Chang, "Biodegradeable semipermeable microcapsules containing enzymes, hormones, vaccines and other biologicals", *J. Bioengineering,* 1, 25–32 (1976), and in EPO Application No. 82300416.3, filed Jan. 27, 1982. However, the delivery of large polypeptides from polylactide matrices has been very difficult to achieve, for reasons that will be further discussed. Of the publications cited above, only the latter two disclose devices containing polypeptides having molecular weights of 2500 or greater.

Polylactide and poly(lactide-co-glycolide) polymers and copolymers (referred to generically hereinafter as polylactide or PLGA polymers) are not soluble in water. In contrast, most polypeptides are soluble in water but not in organic solvents. For this reason, the preparation of polylactide devices in which polypeptide particles are dispersed has, until now, generally followed one of two basic techniques. One technique involves mixing of the components with the polylactide in the molten state followed by heat extrusion, heat pressing, or casting. The second technique involves the creation of a solution/suspension of the polymer and polypeptide in an organic solvent, which is then pour-cast into a film or slab and the solvent evaporated. The latter method usually requires extensive or rapid stirring of the solution/suspension in order to achieve an acceptable degree of uniformity of the polypeptide particles and homogeneity of the polypeptide/polylactide matrix upon solidification. Evaporation of the solvent takes place over several hours to several days unless the film or slab is dried under vacuum, in which case bubbles are invariably created as the solid dries. Additionally, polylactide formulations prepared in this way are not sufficiently uniform for most therapeutic applications; due to coalescence of the water-soluble particle phase, the polypeptide is unevenly distributed within the polylactide as large aggregates of particles. Therefore, formulations prepared in this way must be submitted to further homogenization procedures such as grinding the formulation to a powder and reforming it under heat, or compressing or extruding the formulation under heat. The temperature required for these manipulations is usually at least 70° C.

It is also known to make injectable microcapsules of drug in polylactide. Such microcapsules can be prepared by basic techniques such as that set out in U.S. Pat. No. 3,773,919, and in U.S. application Ser. No. 699,715. The latter method involves dissolving the polymer in a halogenated hydrocarbon solvent, dispersing the aqueous polypeptide containing solution by rapid stirring in the polymer-solvent solution, and adding a non-solvent coacervation agent which causes the polymeric excipient to precipitate out of the halogenated hydrocarbon solvent onto the dispersed polypeptide containing water droplets, thereby encapsulating the polypeptide. The resulting microcapsules are then dried by repeated organic solvent washings.

However, large polypeptides are particularly susceptible to physical and chemical denaturation and consequent loss of biological potency from exposure to excessive heat, solvents, and shear forces. For this reason, incorporation of large polypeptides in polylactide polymers has, until now, required either compromise in the degree of uniformity of the polypeptide/polymer dispersion, or has resulted in substantial loss of the biological potency of the polypeptide, or both. The resultant formulations are generally non-uniform dispersions containing irregularly sized large particles of polypeptide of reduced potency. The incorporation of large and irregular particles of polypeptide causes an uneven rate of drug delivery, and tends to exacerbate the multiphasic release profiles generally associated with polylactide pharmaceutical preparations.

Preparation of more homogenous monolithic formulations by known techniques, such as mixing of the molten components, grinding, and heat homogenation techniques such as compression and extrusion may result in a substantial, often nearly complete loss of biological activity of the polypeptide. For example, a PLGA/interferon formulation formed by heated mixing and extrusion under mild conditions retains less than 1% of the original biological activity of the interferon. (See Example 7, below.) To compensate for the loss in biological activity during manufacturing processes of this type, a large excess of polypeptide must be incorporated in the formulation.

A further disadvantage of formulations which contain denatured polypeptides is the increased immunogenicity which they exhibit. Antibody formation in response to the denatured polypeptide may partially or entirely contravene the desired therapeutic effect.

Accordingly, there is a need for a homogeneous polylactide device which provides controlled and regular delivery of macromolecular polypeptides and can be manufactured without significant loss of biological activity.

SUMMARY OF THE INVENTION

The present invention provides a novel active agent delivery system for the controlled administration of a macromolecular polypeptide to a mammal. The system comprises a polymeric matrix comprising not more than about 30 percent by weight of particles of macromolecular polypeptide and other optional water-soluble components dispersed in a polylactide matrix, wherein substantially all of the particles of polypeptide and other water-soluble components have diameters of $10\mu$ or less and are uniformly and discretely dispersed throughout the matrix, and wherein the polypeptide retains at least about 50 percent of the biological activity which it possessed prior to manufacture of the matrix.

This device provides an economical and reliable method of delivering controlled and regular quantities of biologically active macromolecular polypeptides to body sites which are capable of making available intracellular and or extracellular fluids for transfer into the device. The system can be designed to deliver the active agent at an appropriate rate over prolonged periods of time ranging from less than one day to several months. Generally, active agent release periods of about one week to three months are contemplated.

An important advantage of this controlled release device resides in the fact that it can be manufactured with only minor loss of biological activity of the polypeptide active agent. Maintenance of high biological activity permits the device to be manufactured to contain relatively low initial amounts of the polypeptide.

As a result of maintaining high biological activity of the peptide during manufacture, several further advantages are achieved. First, there is a significant economic advantage to the manufacturer with respect to the cost of active agent incorporated in each dosage form or delivery system. Second, due to the relatively low percentage of polypeptide and other water-soluble components in the device, the contribution of these components to the hydration of the system in vivo is minimized, thereby providing a more constant rate of polypeptide release throughout the entire operational life of the device than can be obtained with previously known biodegradeable systems. Third, the absence of significant quantities of denatured polypeptide reduces the likelihood of undesirable immune responses at the site of polypeptide delivery.

Another important advantage of the controlled release device of this invention resides in the novel physical structure of the polymer/polypeptide matrix. The matrix comprises a very fine dispersion, or micro-suspension, of water soluble components in a polylactide polymer, wherein substantially all of the particles of active agent and any other optionally present water soluble components have diameters of $10\mu$ or less. These particles are uniformly and discretely dispersed throughout the polymer, providing an essentially homogeneous and monolithic device. As with previously known systems, the biologically active polypeptide is released through a combination of diffusion and dissolution mechanisms as the device hydrates and subsequently erodes. However, unlike known polymeric matrix systems which deliver macromolecules, the system of this invention does not rely on the formation of aqueous channels, or macropores, in the matrix for release of the macromolecules from the system. The requirement of macropore formation for drug release to occur is known to result in a triphasic release profile characterized by a middle quiescent phase during which little or no drug is released. There may also be a quiescent, or dead period before the initial phase of drug release. In contrast, because the polypeptide and other water soluble components of this invention are present as very small and discrete particles within the polylactide matrix, aqueous channels are not formed, if at all, until relatively late in the release period. As a result, a very regular release profile is achieved which can be made to begin with very little initial lag time, and which is continuous throughout the life of the system.

Another aspect of the invention resides in a method of administering a macromolecular polypeptide active agent, which comprises placing an appropriately sized and shaped device of the above description at a body site which is capable of making available its intracellular and/or extracellular fluids for absorption by the implant. Further aspects of the invention involve novel methods of preparing the devices described and claimed herein.

BRIEF DESCRIPTION OF THE DRAWING

FIG. I is a graph of the data obtained from the test described in Example 3, and shows the release profiles of $\beta$-interferon from active agent delivery systems implanted subcutaneously in mice over a period of 60 to 100 days. The systems were prepared according to the invention as described in Examples 1 and 2.

DETAILED DESCRIPTION AND PREFERRED EMBODIMENTS

DEFINITIONS

The term "biologically active macromolecular polypeptide" refers to any polypeptide having a molecular weight of not less than about 1000 daltons, preferably not less than about 2500 daltons, which possesses useful biological activity when administered to a mammal.

The phrase "wherein the polypeptide retains at least about 50% of its biological activity" means that at least about 50% of the biological activity potential of the polypeptide will remain at completion of manufacture, as determined within the accuracy of a biological assay for the particular polypeptide such as the one described in Example 5. Generally, the assay will involve spiking the polypeptide loading stock with a known concentration of radioactively labelled polypeptide, extracting the polypeptide from the manufactured system under mild conditions, and determining both the relative radioactivity (counts per minute per ml), and the relative units/ml biological activity, of the loading stock and the extracted polypeptide in a standard biological assay for the polypeptide. The biological assay is performed against a reference standard in serial dilution test wells of the polypeptide samples to be assayed. An arbitrary endpoint is set for scoring the test wells, and the same endpoint is used in scoring the reference samples. The activity of the interferon samples is calculated based on the $\log_{10}$ of the units/ml biological activity of the loading stock equivalent for each extracted sample. Systems which fall within the scope of this invention will demonstrate relative $\log_{10}$ polypeptide activity values which are one/half, or greater, than the $\log_{10}$ units/ml of the corresponding polypeptide loading stock. The preferred embodiments of this invention retain at least about 70% of the biological potential of the polypeptide after manufacture.

The term "substantially all of the particles of polypeptide and other water-soluble components" refers to at a quantity of at least about 75% of the particles of components so identified.

The term "water-soluble components" is used herein to refer to macromolecular polypeptides and other optional pharmaceutically acceptable components which are at least "very slightly soluble" by the definition given in the *United States Pharmacopeia*, XX, page 1121, i.e. having water solubilities of at least 0.1–1.0 mg/ml.

The term "micro-suspension" is used herein to describe particles of polypeptide and other water soluble solid components, substantially all of which have diameters of 10 microns or less, which are substantially uniformly and discretely dispersed throughout the polymer. The term "uniformly and discretely dispersed" is used to indicate that the particles are not touching each other, but rather are individually surrounded by polymer, and are approximately equi-distantly spaced. Determination of the size and distribution of the particles of polypeptide and other water-soluble components can be made by a standard microscopic examination such as that described in Example 4, below. Preferably, substantially all of the particles will have diameters of $5\mu$ or less, and more preferably, $1\mu$ or less.

The term "polylactide" is used herein in a generic sense to describe both homopolymers and copolymers derived from alpha-hydroxycarboxylic acids, particularly α-hydroxyacetic (lactic) and α-hydroxypropionic acid (glycolic) acids. They are usually prepared from the cyclic esters of lactic acids.

The present invention resides in the creation of a homogeneous matrix of a polylactide in which is incorporated a substantially uniform micro-suspension of a biologically active macromolecular polypeptide. The matrix releases the biologically active polypeptide when placed at a body site which can make available its intracellular and/or extracellular fluid for transfer into the device. As the matrix becomes hydrated, the polypeptide is released by diffusion and erosion mechanisms. Because the polypeptides are water-soluble, the rate of release is governed by the rates of hydration and polymer erosion of the device.

The use of polylactide copolymers provides the opportunity to vary the rates of hydration and erosion of the polymer matrix by appropriate choice of the type and relative amount of comonomer used. Some illustrative examples of suitable comonomers include glycolide, β-propiolactone, tetramethylglycolide, β-butyrolactone, 4-butyrolactone, pivalolactone, and intermolecular cyclic esters of α-hydroxy butyric acid, α-hydroxyisobutyric acid, α-hydroxyvaleric acid, α-hydroxyisovaleric acid, α-hydroxy caproic acid, α-hydroxy-α-ethylbutyric acid, α-hydroxyisopcaproic acid, α-hydroxy-3-methylvaleric acid, α-hydroxy-heptanoic acid, α-hydroxyoctanoic acid, α-hydroxydecanoic acid, α-hydroxymysristic acid, α-hydroxystearic acid, and α-hydroxylignoceric acid.

Any of these compounds may be used as a comonomer in the preparation of acceptable polymers. β-butyrolactone can be used as the sole monomer or as the principle monomer along with a suitable comonomer. However it is most preferred to use lactic acid as the sole monomer, or as a copolymer with glycolic acid as the comonomer. The term polylactide is used herein to refer to both to those polymers which are prepared soley from the lactic acid monomer and to those which are prepared as copolymers with other comonomers of the type listed above. The terms poly(lactide-co-glycolide) and PLGA are used interchangeably herein to refer to copolymers which are prepared as copolymers of lactic and glycolic acid.

The alpha hydroxy acid units from which the preferred polymers are prepared may be the optically active (D- and L-) forms or optically inactive (DL-, racemic) forms. For example, lactic acid, whether it is the sole monomer, or a comonomer component, can be present as D-lactic acid, L-lactic acid, DL-lactic acid, or any mixture of D- and L- lactic acids.

The combinations of preferred monomer and comonomer which can be prepared are numerous, but the most useful are those polymers prepared from lactic acid alone or lactic acid and glycolic acid wherein the glycolic acid is present as a comonomer in a molar ratio of lactide to glycolide units of 100:0 to 30:70, preferably 100:0 to 40:60. It is most preferred to use a poly(lactide-co-glycolide) copolymer having a molar ratio of lactide to glycolide of between about 75:25 and 50:50.

Poly(lactide-co-glycolide) polymers preferably will range in molecular weight from about 20,000 to about 100,000 daltons, stated as an average. The molecular weight of a particular copolymer is independent of its monomeric makeup. For example, the preferred 50:50 copolymer can have a molecular weight which falls anywhere within this range.

The invention comprehends the use of polymers which are varied both as to their monomer composition and their molecular weight, including those outside the preferred compositions and ranges given above, provided that the polymer is capable of being formed as a solid material.

For the purposes of this invention the molecular weight of a particular polymer is determined as a function of its intrinsic viscosity as measured in a capillary viscometer using chloroform or haxafluoroisopropanol at 30° C. The intrinsic viscosities of polylactides suitable for use in this invention range from about 0.2 dl/g to about 1.5 dl/g, and are preferably in the range of about 0.33 to 1.0 dl/g.

Methods of preparing polylactides are well documented in the scientific and patent literature. The following patents, the teachings of which are hereby incorporated by reference, provide detailed descriptions of suitable polylactides, their physical properties, and methods of preparing them: U.S. Pat. Nos. 3,773,919, 4,293,539, 3,435,008, 3,442,871, 3,468,853, 3,597,450, 3,781,349, 3,736,646 and copending U.S. application Ser. No. 699,715, filed Feb. 8, 1985.

The macromolecular polypeptides which may be incorporated in the device of this invention are biologically active molecules having molecular weights greater than about 1000, preferably greater than about 2500, more preferably between about 6,000 and 500,000, and most preferably greater than about 10,000. The choice of polypeptides which can be delivered in accordance with the practice of this invention is limited only by the requirement that they be at least very slightly soluble in an aqueous physiological media such as plasma, interstitial fluid, and the intra and extracellular fluids of the subcutaneous space and mucosal tissues. The term "very slightly soluble" refers to a water-solubility of at least about 0.1–1.0 mg/ml, as defined hereinabove.

Exemplary classes of polypeptides include, among others, proteins, enzymes, nucleoproteins, glycoproteins, lipoproteins, hormonally active polypeptides, and synthetic analogues including agonists and antagonists of these molecules.

The protein classes which are suitable for use in this invention are numerous, including immune modulators, lymphokines, monokines, cytokines, enzymes, antibodies, growth promotants, growth inhibitory factors, blood proteins, hormones, vaccines (including viral, bacterial, parasitic, and rickettsial antigens), blood coagulation factors and the like, including various precursor protein forms, muteins, and other analogs.

Specific examples of polypeptides suitable for incorporation in the delivery system of this invention include the following biologically active macromolecules, and muteins and other analogs thereof: interferons ($\alpha$-, $\beta$-, $\gamma$- and muteins thereof such $\beta_{ser17}$), colony stimulating factors (1, 2, 3, GM, $\alpha$-, $\beta$-, $\gamma$-, and the like), interleukins (IL-1, IL-$\alpha$, IL-$\beta$, IL-2, IL-3, IL-4, IL-5, and the like), macrophage activating factors, macrophage peptides, B cell factors (B cell growth factor and the like), T cell factors, protein A, suppressive factor of allergy, suppressor factors, cytotoxic glycoprotein, immunocytotoxic agents, immunotoxins, immunotherapeutic polypeptides, lymphotoxins, tumor necrosis factors ($\alpha$-, $\beta$-, and the like), cachectin, oncostatins, tumor inhibitory factors, transforming growth factors such as TGF-$\alpha$ and TGF-$\beta$), albumin, alpha-1-antitrypsin, apolipoprotein-E, erythroid potentiating factors, erythropoietin, factor VII, factor VIII(c), factor IX, fibrinolytic agent, hemopoietin-1, kidney plasminogen activator, tissue plasminogen activator, urokinase, pro-urokinase, streptokinase, lipocortin, lipomodulin, macrocortin, lung surfactant protein, protein C, protein 5, C-reactive protein, renin inhibitors, collagenase inhibitors, superoxide dismutase, epidermal growth factor, growth hormone, platelet derived growth factor, osteogenic growth factors, atrial naturetic factor, auriculin, atriopeptin, bone morphogenic protein, calcitonin, calcitonin precursor, calcitonin gene-related peptide, cartilage inducing factor, connective tissue activator protein, fertility hormones (follicle stimulating hormone, leutinizing hormone, human chorionic gonadotropin), growth hormone releasing factor, osteogenic protein, insulin, proinsulin, nerve growth factor, parathyroid hormone, parathyroid hormone inhibitors, relaxin, secretin, somatomedin C, insulin-like growth factors, inhibin, adrenocoricotrophic hormone, glucagon, vasoactive intestinal polypeptide, gastric inhibitory peptide, motilin, cholecystokinin, pancreatic polypeptide, gastrin releasing peptide, corticotropin releasing factor, thyroid stimulating hormone, vaccine antigens including antigens of HTLV-I, II, HTLV-III/LAV/HIV (AIDS virus), cytomegalovirus, hepatitis A, B, and non-A/non-B, herpes simplex virus-I, herpes simplex virus II, malaria, pseudorabies, retroviruses, feline leukemia virus, bovine leukemia virus, transmissible gastroenteritis virus, infectious bovine rhinotracheitis, parainfluenza, influenza, rotaviruses, respiratory syncytial virus, varicella zoster virus, Epstein-Barr virus, pertussis, and anti-infective antibodies including monoclonal and polyclonal antibodies to gram negative bacteria, pseudomonas, endotoxin, tetanus toxin, and other bacterial or viral or other infectious organisms.

The lists of macromolecular polypeptides recited above are provided only to illustrate the types of active agents which are suitable for use in practicing the invention, and are not intended to be exclusive.

A particularly preferred class of polypeptides are the naturally occurring and synthetic interferons. Interferons are polypeptides having monomer molecular weights in the range of about 15,000 to about 28,000. They are proteins which are synthesized by mammalian cells in response to viral infection, immune stimulation and other factors. They are presently designated as members of one of three major classes: alpha or leukocyte interferon (IFN-$\alpha$), beta or fibroblast interferon (IFN-$\beta$), and gamma or immune interferon (IFN-$\gamma$). Their biological properties include antiviral, anti-proliferative and immunomodulating activities, which have led to their clinical use as therapeutic agents for the treatment of viral infections and malignancies.

Interferons can be obtained from natural sources such as leukocytes, lymphoblastoid cells in continuous suspension or culture, and fibroblast cultures. T lymphocytes can be stimulated to produce gamma interferon. $\beta$-interferon is derived from mammalian cells such as fibroblast cells. As used herein, "$\beta$-interferon" or "IFN-$\beta$" includes $\beta$-interferon derived both from natural sources, including human, bovine, canine, feline, porcine and equine, and by recombinant DNA techniques. It also includes modified forms of $\beta$-interferon; e.g., by glycosylation, methylation, substitution and/or deletion of a limited number of amino acids. As used herein, HuIFN-$\beta$ refers to human $\beta$-interferon, and rHuIFN-$\beta$ refers to HuIFN-$\beta$ produced using recombinant techniques. IFN-$\beta_{ser-17}$ refers to $\beta$-interferon in which the seventeenth amino acid has been replaced with serine.

Interferon concentrations are commonly expressed as standard "units" which are internationally accepted and documented, and relate to the potency of a given quantity of interferon to inhibit virus replication under standard conditions.

IFN-$\beta_{ser-17}$ is best produced by modifying DNA sequences which code for IFN-$\beta$, and then manipulating microorganisms to express the modified DNA as protein. When the first base of codon 17 (thymine) of the sense strand of the DNA sequence which codes for the mature IFN-$\beta$ is replaced with adenine, the cysteine residue at position 17 in the amino acid sequence of IFN-$\beta$ is replaced by serine. By changing T to other bases, and by changing other bases in codon 17, cysteine may be replaced with other amino acids. The site-specific mutagenesis is induced using a synthetic 17-nucleotide primer having the sequence GCAATTTT-CAGAGTCAG which is identical to a seventeen nucleotide sequence on the sense strand of IFN-$\beta$ in the region of codon 17 except for a single base mismatch at the first base of codon 17. (As used in this context herein, C is deoxycytidine, T is deoxythymidine, A is deoxyadenosine, and G is deoxyguanosine.) The mismatch is at nucleotide 12 in the primer. The 17-mer is hybridized to single-stranded M13 phage DNA which carries the antisense strand of the IFN-$\beta$ gene. The oligonucleotide primer is then extended on the DNA using DNA polymerase I Klenow fragment (a fragment of DNA polymerase I lacking the 5'-exonuclease subunit) and the resulting double-strand DNA (dsDNA) is converted to closed circular DNA with T4 ligase. Replication of the resulting mutational heteroduplex yields clones from the DNA strand containing the mismatch. Mutant clones may be identified and screened by the appearance or disappearance of specific restriction sites, antibiotic resistance or sensitivity, or by other methods known in the art. When cysteine is substituted by serine, the substitution of T by A results in the creation of a new HinfI restriction site in the structural gene. (A restriction site is a point in a DNA sequence that is recognized and cleaved by a particular restriction enzyme. A HinfI restriction site is a restriction site recognized by HinfI endonuclease.) The mutant clone is identified by using the oligonucleotide primer as a probe in a hybridization screening of the mutated phage plaques. The primer will have a single mismatch when hybridized to the parent but will have a perfect match when hybridized to the mutated phage DNA. Hybridization conditions can then be devised where the oligonucleotide primer will preferentially hybridize to the mutated DNA but not to the parent DNA. The newly generated HinfI site also serves as a means of confirming the single base mutation in the IFN-$\beta$ gene.

The M13 phage DNA carrying the mutated gene is isolated and spliced into an appropriate expression vector such as plasmid pTrp3, and a host such as *E. coli* strain MM294 is then transformed with the vector. Suitable growth media for culturing the transformants and their progeny are known to those skilled in the art. The expressed mutein (protein derived from a mutated gene) of IFN-$\beta$ is isolated, purified and characterized. Further description of this method of synthesizing IFN-B can be found in U.S. Pat. No. 4,518,814, the teachings of which are incorporated herein by reference. U.S. Pat. No. 4,518,584 also discloses muteins of $\beta$-IFN and interleukin-2, and teaches methods of preparing them.

Recombinant DNA techniques for producing interferons of the $\alpha$-and $\gamma$-classes, as well as muteins of interferons are also known. Nagata et al., in *Nature* 284: 316–320 (1980) teaches a method of preparing bacteria which express $\alpha$-interferon. $\gamma$-Interferon can be produced by the method disclosed in EPO application No. 0138087A, and corresponding U.S. application Ser. No. 534,04, filed Sept. 20, 1983, the teachings of which are incorporated herein by reference.

In addition to incorporating one or more biologically active macromolecular polypeptides, the controlled release device of this invention may contain other water soluble, pharmaceutically acceptable components. The optional water-soluble components which may be incorporated in the polylactide matrix are present as particles having diameters of about 10 microns or less. If present, they are intimately mixed with the macromolecular polypeptides, and are uniformly and discretely dispersed throughout the polymer.

Most macromolecular polypeptides benefit from the presence of small quantities of stabilizers, buffers, salts and the like. Water-soluble components which may be useful in the practice of this invention include, but are not limited to other active agents, proteins or other polypeptides, stabilizers, carbohydrates, buffers, salts, surfactants and plasticizers. Examples of suitable stabilizers include human serum albumin (HSA), gelatin, dextrose, other carbohydrates. Examples of other carbohydrates suitable for incorporation in this invention include sucrose, maltose, mannose, glucose, fructose, lactose, sorbitol and glycerol. Suitable surfactants include Tween (e.g. Tween-20, Tween-80), Pluronic® polyols such as Pluronic® L101, L121 and F127. Among the suitable plasticizers are the polyethylene glycols, glycerides and ethylcellulose.

The relative proportions of macromolecular polypeptide and other-water soluble components to polylactide and water-insoluble components within the matrix can be varied depending on the polypeptide to be administered and the desired rate and duration of release. The macromolecular active agent and other water-soluble components may comprise up to about 30 weight percent of the system. The precise amount will depend on such factors as the potency of the particular active agent, its physiochemical and pharmacokinetic behaviour, its stability and the desired duration of release.

A preferred composition for the polylactide matrix comprises, by weight:
(a) 80 to 99.9999% polylactide; and
(b) 0.0001 to 20% biologically active macromolecular polypeptide and other optional water-soluble components. For very active polypeptides, the total amount of polypeptide and other water-soluble components may be as low as 10%, 5%, 2% or less of the total weight of the matrix.

The present invention is well-suited to the controlled delivery of interferons. The amount of interferon incorporated in the polylatide matrix will preferably be 20%, or less, depending on the particular interferon and the other factors listed above. A presently preferred composition comprises, by weight:
(a) 90 to 99.999% polylactide; and
(b) 0.001 to 2% HuIFN-$\beta$, and may include up to about 10% of other water-soluble components.

A more preferred composition comprises, by weight:
(a) 95 to 99.9 percent polylactide;
(b) 0.01 to 0.1 percent HuIFN-$\beta$, and may include up to about 5% of other water-soluble components.

A particularly preferred composition comprises, by weight:
(a) 97.47 percent poly(lactide-co-glycolide) having a molar ratio of 50:50 and an intrinsic viscosity of about 0.64 dl/g;
(b) 0.03 percent HuIFN-$\beta$;
(c) 1.25 percent human serum albumin; and
(d) 1.25 percent dextrose.

The preferred interferon for incorporation in the foregoing systems is rHuIFN-$\beta_{ser17}$.

METHODS OF PREPARATION

The delivery systems of this invention may be fabricated by any method which achieves the desired microsuspension conformation and substantially maintains the biological activity of the macromolecular polypeptide. A preferred method involves spray-casting of a microsuspension of the polypeptide in a solution of the polylactide. The skilled chemist will comprehend various methods by which the micro-suspension can be made. Two novel and useful methods are described below.

Acetone Method

An aqueous, buffered solution of the macromolecular polypeptide and other optional water-soluble components buffer is added to a solution of the chosen polylactide in acetone at room temperature. The resulting mixture is vortexed at high speed using a standard laboratory vortex mixer for approximately 5 to 120, preferably about 10, seconds. A precipitate of the polymer, polypeptide, and other components is formed which is then centrifuged for about 0.5 to 30 minutes, preferably about 10 minutes, at 500 to 1000, preferably 700×g. The resulting supernatant of acetone and water is removed, additional acetone added, and the mixture vortexed at high speed until the PLGA in the pellet is dissolved, leaving a micro-suspension of polypeptide and other water-soluble components in the solution of PLGA in acetone.

Methylene Dichloride Method

An aqueous, buffered solution of the polypeptide and other optional water-soluble components is added to a solution of the chosen polylactide in methylene dichloride. The resulting mixture is vortexed for approximately 10 to 180 seconds, preferably about 60 seconds, at high speed, until a white emulsion is formed. The emulsion is immediately transferred to an airbrush or other suitable spray device and spray cast as described below.

Formation of the Active Agent Delivery Systems

The active agent delivery systems of this invention are formed so that the final solid polypeptide/polylactide matrix product possesses the required micro-suspension morphology in which substantially all of the particles of polypeptide and other water-soluble components have diameters of 10μ or less and are uniformly and discretely dispersed throughout the matrix. To assure that the liquid micro-suspension of water-soluble components in the polymer solution does not coalesce into a suspension of larger particles upon solidification of the formulation, it is preferable to promptly spray-cast the micro-suspension onto a non-stick surface with an airbrush or other suitable device using appropriate conditions. The airbrush is preferably held about 4 to 6 inches from the surface of the sheet and the film sprayed with a constant motion to achieve an even film. Suitable non-stick surfaces include polypropylene, teflon, nylon, polyethylene or derivatives thereof, and other materials with similar non-stick properties. Polypropylene, teflon and polyethylene are preferred. The spray-cast film can be made as thin as about 5 microns and as thick as 1000 microns. For films thicker than about 100 microns it is preferable to allow some time for drying between repeated spray-castings of layers. Thinner films (about 10 to 50 microns) are preferred when it is desirable to minimize the exposure of the polypeptide to the organic solvent. Generally, the resulting film should be allowed to dry completely before being configured into the final controlled release device or system. Depending on the thickness of the film, the drying time to achieve complete dryness will vary from less than one hour to about three days, and can be shortened if desired by drying under vacuum after the matrix has solidified to the point where bubbles will not be caused.

For many polypeptides, parenteral injection is a preferred route of administration. The polypeptide/polylactide matrix formulation of this invention can be prepared in an injectable form by atomizing the liquid micro-suspension and drying the resulting micro-particles in a counter-current or vortex of air or inert gas. The resulting particles can be injected directly, or can be incorporated in a compatible and pharmaceutically acceptable injectable solution or suspension.

The controlled delivery systems of this invention may be structurally reinforced with an inert, pharmaceutically acceptable material such as a fine silk mesh, teflon mesh or other surgically inert material. It is especially advantageous to incorporate a reinforcement material when it is anticipated that the controlled release device will need to be recovered from its active delivery site. Reinforced devices may be made by spraying the polypeptide/polylactide micro-suspension onto the reinforcement material, which is preferably resting on a non-stick surface. The film is then allowed to dry briefly, and can be turned over, and sprayed on the other side. This procedure is repeated until a film of the desired thickness is achieved. Preferably, the texture of the reinforcement material will be completely covered by a smooth layer of the polymer.

The polymeric film obtained by spray-casting as described above can be configured into any solid article suitable for the intended site of use. For example, the film can be cut into pieces of known dimensions and implanted subcutaneously as single segments. Alternatively, the film can be rolled into a cylindrical device of desired dimensions. Multiple layers of film can be laminated and die-cut to create devices of virtually any size and shape. Integrity of the layers can be assured by light spraying or brushing between lamination of layers with a suitable solvent for the polymer or exposure to solvent vapor.

The controlled release devices of this invention can be designed to deliver the biologically active macromolecular polypeptide, and any accompanying active agents, at a controlled rate over a prolonged period of time ranging from less than one day to several months. Examples of devices which delivered therapeutically useful levels of β-interferon subcutaneously over a period of 60 to 100 days are described in Examples 1 and 2 and shown in FIG. I. The actual rate and duration of release can be varied within the practice of this invention by the choice of polylactide polymer (e.g. choice of monomer or comonomers, molar ratio and intrinsic viscosity) or copolymer, by the shape and configuration of the device (e.g. flat, rolled, single layer or multiple layer), and to a lesser extent, by the amount of active agent which is incorporated.

The amount of active agent incorporated in the device can vary between 0.0001 and 30 percent, by weight, of the polymeric system. The optimal amount for any given system will depend on the potency of the agent, the desired physiologic effect, the intended length of treatment, and the rate of active agent release. Preferably, the devices of this invention contain about 0.0001 to 20 percent, by weight, of the macromolecular polypeptide.

The size of the device will likewise depend on the amount of active agent which it contains, its release rate, and the intended duration of treatment. For example, if it is known that a particular polypeptide/polylactide formulation releases the polypeptide at an average rate of $10^6$ units per day, and the desired duration of treatment is 60 days, the device would require a loading of at least $6 \times 10^7$ units of polypeptide. Based on the weight percent polypeptide in the system, the required size of the device can be calculated.

The following preparations and examples are provided to further illustrate the practice of this invention, and are not intended to in any way limit its scope.

PREPARATION 1

Cloning of the IFN-β gene into M13 Vector

The use of M13 phage vector as a source of single-stranded DNA template has been demonstrated by G. F. Temple et al *Nature* (1982) 296:537–540. Plasmid pβ trp containing the IFN-β gene, under control of *E. coli* trp promoter, is digested with the restriction enzymes HindIII and XhoII. The M13mp8 (J. Messing, "Third Cleveland Symposium on Macromolecules: Recombinant DNA," Ed. A. Walton, Elsevier Press, 143–153 (1981) replicative form (RF) DNA is digested with restriction enzymes HindIII and BamHI and mixed with the pβ1 trp DNA which have previously been digested with HinDIII and XhoII. The mixture is then ligated with T4 DNA ligase and the ligated DNA transformed into competent cells of *E. coli* strain JM 103 and plated on Xgal indicator plates (J. Messing et al, *Nucleic Acids Res* (1981) 9:309–321). Plaques containing recombinant phage (white plaques) are picked, inoculated into a fresh culture of JM 103 and minipreps of RF molecules prepared from the infected cells (H. D. Birnboim and J. Doly, *Nucleic Acid* Res. (1979) 7:1513–1523). The RF molecules are digested with various restriction enzymes to identify the clones containing the IFN-β insert. Single-stranded (ss) phage DNA is prepared from clone M13-β1 to serve as a template for site-specific mutagenesis using a synthetic oligonucleotide.

PREPARATION 2

Site specific mutagenesis

Forty picomoles of the synthetic oligonucleotide GCAATTTTCAGAGTCAG (primer) is treated with T4 kinase in the presence of 0.1 mM adenosine triphosphate (ATP). 50 mM hydroxymethylaminomethane hydrochloride (Tris-HCl) pH 8.0, 10 mM $MgCl_2$, 5 mM dithiothreitol (DTT) and 9 units of T4 kinase, in 50 μl at 37° C. for 1 hr. The kinased primer (12 pmole) is hybridized to 5 μg of ss M13-β1 DNA in 50 μl of a mixture containing 50 mM NaCl, 10 mM tris-HCl, pH 8.0, 10 mM $MgCl_2$ and 10 mM β-mercaptoethanol by heating at 67° C. for 5 min and at 42° C. for 25 min. The annealed mixture is then chilled on ice and then added to 50 μl of a reaction mixture containing 0.5 mM each of deoxynucleotide triphosphate (dNTP), 80 mM Tris-HCl, pH 7.4, 8 mM $MgCl_2$, 100 mM NaCl, 9 units of DNA polymerase I Klenow fragment, 0.5 mM ATP and 2 units of T4 DNA ligase, incubated at 37° C. for 3 hr and at 25° C. for 2 hr. The reaction is then terminated by phenol extraction and ethanol precipitation. The DNA is dissolved in 10 mM Tris-HCl pH 8.0, 10 mM ethylenediaminetetraacetic acid (EDTA), 50% sucrose and 0.05% bromophenylblue and electrophoresed on 0.8% agarose gel in the presence of 2 μg/ml of ethidium bromide. The DNA bands corresponding to the RF forms of M13-β1 are eluted from gel slices by the perchlorate method (R. W. Davis, et al, "Advanced Bacterial Genetics," Cold Spring Harbor Laboratory, N.Y., p. 178–179 (1980)). The eluted DNA is used to transform competent JM 103 cells, grown overnight and single strand (ss) DNA isolated from the culture supernatant. This ssDNA is used as a template in a second cycle of primer extension, the gel purified RF forms of the DNA are transformed into competent JM 103 cells, plated onto agar plates and incubated overnight to obtain phage plaques.

PREPARATION 3

Screening and identification of mutagenized plaques

Plates containing mutated M13-β1 plaques as well as two plates containing unmutated M13-β1 phage plaques are chilled to 4° C., and plaques from each plate transferred onto two nitrocellulose filter circles by layering a dry filter on the agar plate for 5 min for the first filter and 15 min for the second filter. The filters are then placed on thick filter papers soaked in 0.2N NaOH, 1.5M NaCl and 0.2% Triton X-100 for 5 min. and neutralized by layering onto filter papers soaked with 0.5M Tris-HCl, pH 7.5 and 1.5M NaCl for another 5 min. The filters are washed in a similar fashion twice on filters soaked in 2xSSC (standard saline citrate), dried and then baked in a vacuum oven at 80° C. for 2 hr. The duplicate filters are prehybridized at 55° C. for 4 hr. with 10 ml per filter of DNA hybridization buffer (5xSSC) pH 7.0 4xDenhardt's solution (polyvinyl-pyrrolidine, ficoll and bovine serum albumin, 1x=0.02% of each), 0.1% sodium dodecyl sulfate (SDS), 50 mM sodium phosphate buffer pH 7.0 and 100 μg/ml of denatured salmon sperm DNA. A $^{32}P$-labeled probe is prepared by kinasing the oligonucleotide primer with $^{32}P$-labeled ATP. The filters are hybridized to $3.5 \times 10^5$ cpm/ml of $^{32}P$-labeled primer in 5 ml per filter of DNA hybridization buffer at 55° C. for 24 hr. The filters are washed at 55° C. for 30 min. each in washing buffers containing 0.1% SDS and decreasing amounts of SSC. The filters are washed initially with buffer containing 2xSSC and the control filters containing unmutated M13-β1 plaques are checked for the presence of any radioactivity. The concentration of SSC is lowered stepwise and the filters washed until no detectable radioactivity remains on the control filters with the unmutated M13-β1 plaques. The filters are air dried and autoradiographed at −70° C. for 2–3 days.

PREPARATION 4

Expression of mutated IFN-β in E. coli

RF DNA from M13-SY2501 is digested with restriction enzymes HindIII and XhoII and the 520 bp insert fragment purified on a 1% agarose gel. The plasmid pTrp3 containing the *E. coli* trp promoter is digested with the enzymes HindIII and BamHI, mixed with the purified M13-SY2501 DNA fragment and ligated in the presence of T4DNA ligase. The ligated DNA is transformed into *E. coli* strain MM294. Ampicillin resistant transformants are screened for sensitivity to the drug tetracycline. Plasmid DNA from five ampicillin resistant, tetracycline-sensitive clones are digested with HinfI to screen for the presence of the M13-SY2501 insert.

The plasmid designated as clone pSY2501 is available from the Agricultural Research Culture Collection (NRRL), Fermentation Laboratory, Northern Regional Research Center, Science and Education Administration, U.S. Department of Agriculture, 1815 North University Street, Peoria, Ill. 60604 and is assigned accession numbers CMCC No. 1533 and NRRL No. B-15356.

Cultures of pSY2501 and pβltrp are grown up to an optical density ($DD_{600}$) of 1.0. Cell free extracts are prepared and the amount of IFN-β antiviral activity assayed on GM2767 cells in a microtiter assay.

PREPARATION 5

Purification of IFN-$\beta_{ser17}$

IFN-$\beta_{ser17}$ is recovered from E. coli which have been transformed to produce IFN-$\beta_{ser17}$. The E. coli are grown in the following growth medium to an OD of 10–11 at 680 nm (dry wt 8.4 g/l).

| Ingredient | Concentration |
| --- | --- |
| $NH_4Cl$ | 20 mM |
| $K_2SO_4$ | 16.1 mM |
| $KH_2PO_4$ | 7.8 mM |
| $Na_2HPO_4$ | 12.2 mM |
| $MgSO_4.7H_2O$ | 3 mM |
| $Na_2citrate.2H_2O$ | 1.5 mM |
| $MnSO_4.4H_2O$ | 30 $\mu$M |
| $ZnSO_4.7H_2O$ | 30 $\mu$M |
| $CuSO_4.5H_2O$ | 3 $\mu$M |
| L-tryptophan | 70 mg/l |
| $FeSO_4.7H_2O$ | 72 $\mu$M |
| thiamine HCl | 20 mg/l |
| qlucose | 40 G/L |
| pH controlled with $NH_4OH$ | |

A 9.9 l (9.9 kg) harvest of the transformed E. coli is cooled to 20° C. and concentrated by passing the harvest through a cross-flow filter at an average pressure drop of 110 kPa and steadystate filtrate flow rate of 260 ml/min until the filtrate weight is 8.8 kg. The concentrate (approximately one liter) is drained into a vessel and cooled to 15° C. The cells in the concentrate are then disrupted by passing the concentrate through a Mason-Gaulin homogenizer at 5° C. 69,000 kPa. The homogenizer is washed with one liter phosphate buffered saline, pH 7.4 (PBS), and the wash is added to the disruptate to give a final volume of two liters. This volume is continuously centrifuged at 12000xg at a 50 ml/min flow rate. The solid is separated from the supernatant and resuspended in four liters of PBS containing 2% by wt. SDS. This suspension is stirred at room temperature for 15 min after which there should be no visible suspended material. The solution is then extracted with 2-butanol at a 1:1 2-butanol:solution volume ratio. The extraction is carried out in a liquid-liquid phase separator using a flow rate of 200 ml/min. The organic phase is then separated and evaporated to dryness to yield 21.3 g of protein. This may then be resuspended in distilled water at a 1:10 volume ratio.

EXAMPLE I

Preparation of Controlled Release Devices Containing Interferon (Acetone Method)

A. Preparation of IFN/PLGA Micro-suspension

One gram of D,L-PLGA (molar ratio 50:50, inherent viscosity 0.64 dl/g) was dissolved in 5 ml acetone at room temperature. 0.3 mg of recombinant HuIFN-$\beta$ in 1 ml of buffer was added to the PLGA in acetone and the resulting mixture was vortexed at high speed for approximately 30 seconds. The precipitate of PLGA, HSA, IFN and possibly dextrose which formed was then centrifuged for 10 minutes at 700 X g. The supernatant of acetone and water was removed with a pipet and the residual liquid removed with a cotton swab. Ten ml acetone was added, and the mixture was centrifuged at high speed until the PLGA in the pellet was dissolved, leaving a micro-suspension of HuIFN-$\beta$, HSA and dextrose in a solution of PLGA in acetone.

B. Spray-Casting of the IFN/PLGA Micro-suspension

The resulting IFN/PLGA micro-suspension, obtained as described in paragraph A, was sprayed with an airbrush, using compressed air at 15 PSI, onto a clean polyethylene sheet. The airbrush was held 4 to 6 inches from the surface of the sheet and the film sprayed with a constant motion to achieve an even film of the PLGA formulation which was approximately 50 microns thick.

C. Reinforcement of Film

Using IFN/PLGA micro-suspension from paragraph A, a spray-cast film with silk reinforcement was prepared as follows:

Fine woven silk mesh was stretched on a frame and the stretched portion brushed with a solution of 100 mg/ml PLGA (molar ratio 50:50, intrinsic viscosity 0.64) in acetone. The wet mesh was allowed to dry, and then brushed with repeated applications of PLGA solution until the pores in the silk mesh were completely filled. The mesh was then dried, placed on a polyethylene sheet, and spray-cast with the IFN/PLGA micro-suspension. After drying for one hour, the coated mesh was turned over, coated side down, and again sprayed with the IFN/PLGA micro-suspension, applying a layer of polymer about 100 microns thick. After drying for another hour, the previously coated side was again sprayed, allowed to dry, turned over, and the second side sprayed again. The resulting film had a thickness of 300 microns. D. The films obtained in paragraphs B and C were stored at room temperature for 18 hours. They were then removed from the polyethylene sheet and dried at room temperature for three days.

E. Device Configuration

Using spray-cast film obtained as described in paragraphs A–D, above, controlled release devices were configured as follows:

a. Flat film segments, 1×2 cm, were cut from the non-reinforced film.

b. Flat film segments, 1×2 cm, were cut from the reinforced film.

c. Flat film segments, 3×5 cm, were cut from non-reinforced film, were rolled on an 18 guage wire and the film secured by a very light application of acetone with a cotton swab to the final 5 mm length, or by exposure to acetone vapor. The wire was removed and the rolls sliced into lengths of 5 or 10 mm.

d. Flat film segments, 3×5 cm, were cut from reinforced film, were rolled on an 18 guage wire and the film secured by a very light application of acetone with a cotton swab to the final 5 mm length, or by exposure to acetone vapor. The wire was removed and the rolls sliced into lengths of 5 or 10 mm.

The release profiles of these devices when implanted subcutaneously in mice over a period of 100 days are shown and identified in FIG. I as devices 1, 2, and 3 for configurations a, b, and c respectively.

EXAMPLE 2

Preparation of Controlled Release Devices Containing Interferon (Methylene Dichloride Method)

One gram of D,L-PLGA (molar ratio 50:50, intrinsic viscosity 0.64 dl/g) was dissolved in 4 ml methylene dichloride. 0.3 mg of recombinant HuIFN-$\beta$ in 1 ml of buffer containing 12.5 mg/ml human serum albumin (HSA) and 12.5 mg/ml dextrose was added to the dissolved PLGA solution. The resulting mixture was vortexed for approximately 60 seconds at high speed until a white emulsion was formed. The emulsion was immediately transferred to an airbrush and sprayed onto a polyethylene film, and dried in the same manner as described in Example 1, paragraph D.

Controlled release devices were configured by rolling 3 cm×5 cm film segments on an 18 guage wire, securing the end of the roll by exposure to acetone, removal of the wire, and slicing of each roll into 5 and 10 mm lengths.

The release profile of these devices when implanted subcutaneously in mice over a period of 60-100 days is shown as device 4 in FIG. I.

EXAMPLE 3

Determination of In Vivo Release Profile When Implanted Subcutaneously In Mice

A. Release profile of $\beta$-Interferon

Sixty of each of devices 1-4 were prepared as described in Examples 1 and 2, but the HuIFN-$\beta$ was spiked with radioactively-labelled $\beta$-interferon ($^{125}$I-rHuIFN-$\beta_{ser17}$). The devices were sterilized with 1.25 Mrads of gamma-irradiation and implanted subcutaneously in the dorsal region of ICR female mice weighing 18-20 gm. One device wes implanted in each mouse. After varying intervals of time (1 to 100 days), the devices were removed from the mice and the radioactivity of the remaining $^{125}$I-rHuIFN-$\beta_{ser17}$ was determined. FIG. I shows release profiles of devices 1-4 over a period of up to 100 days in vivo.

EXAMPLE 4

Determination of Particle Size and Distribution

PLGA/IFN films prepared as described in Examples 1 and 2, above, were analyzed to determine the particle size of the interferon and other macromolecules (human serum albumin and dextrose) in each formulation, according to the following procedures:

A. PLGA/IFN films prepared as described in Example 1

One gram of D,L-PLGA (molar ratio 50:50, intrinsic viscosity 0.64 dl/g) was dissolved in 5 ml acetone at room temperature. 0.3 mg of recombinant HuIFN-$\beta$ in 1 ml of buffer containing 12.5 mg HSA and 12.5 mg dextrose was added to the PLGA in acetone and the mixture was vortexed at high speed for approximately 10 seconds. The precipitate of PLGA, HSA, IFN and possibly dextrose which formed was then centrifuged for 10 minutes at 700× g. The supernatant of acetone and water was removed with a pipet and the residual liquid removed with a cotton swab. Ten ml acetone were added, and the resulting mixture centrifuged at high speed until the PLGA in the pellet was dissolved, leaving an IFN, HSA, dextrose precipitate suspended in PLGA dissolved in acetone. A drop of the suspension was viewed under a polarizing light microscope on a glass slide with cover slip at 100× magnification using an ocular reticle with 10 micrometer divisions.

The particle sizes of the solid macromolecular components (IFN, HSA, dextrose) suspended in the PLGA/acetone solution ranged from less than or equal to the limit of detection (approximately 100 to 500 nanometers) to 100 microns. Particles having diameters of greater than 10 microns were less than 10% of the total number of particles, and most of the particles had diameters of less than 1 micron. Less than 10% of the visible particles could be observed to be touching at least one other particle.

B. PLGA/IFN films prepared as described in Example 2

A drop of the PLGA/IFN micro-suspension prepared according to the method described in Example 2 above was viewed under a polarizing light microscope on a glass slide with cover slip at 100× magnification using an ocular reticle with 10 micrometer divisions. No particles were observed at 100× magnification, indicating that all of the IFN and HSA had particle sizes of less than or equal to the limit of detection (100 to 500 nanometers).

EXAMPLE 5

Assay of Interferon Biological Antiviral Activity

The assay for interferon biological antiviral activity measures the effect interferon exerts on cells by monitoring their inhibition of the cytopathic effect of vesicular stomatitis virus (VSV) in human wish cells. Virus caused cell damage can be visualized in the light microscope. In cells that are incubated with active interferon, virus growth is reduced. The units of active interferon are determined as reciprocals of endpoint dilutions of an interferon preparation, and the endpoint is defined as the dilution of interferon which inhibits growth of virus by about fifty percent.

The interferon contained in controlled release systems prepared as described in Examples 1 and 2 and spiked with a known concentration of [$^{125}$I]rHuIFN-$\beta_{ser17}$ was extracted from the systems as described in Example 6, below. The extracted interferon samples were assayed to determine the biological activity of the interferon in manufactured systems relative to the biological activity of the loading stock interferon, as described in paragraphs A-D, below.

A. Method

25 $\mu$l of each interferon sample to be assayed and the reference material are pipeted individually into a row of wells of a sterile 96 well microtiter plate containing 50 $\mu$l Eagle's minimum essential media (EMEM) per well. The reference material is the international standard of HuIFN-$\beta$ from the National Institutes of Health, Ref. No. G-023-902-527. Each sample is tested in duplicate, and one row column of each plate is reserved for controls to which are added an additional 25 $\mu$l EMEM. The plates are then treated under UV light for 6 minutes to prevent bacterial growth. Serial three-fold dilutions (standard one-half log$_{10}$ dilutions) of each sample are then prepared in the remaining wells of the microtiter plate by dilution with EMEM to obtain 50 $\mu$l of diluted sample in each well. 50 $\mu$l of 2% fetal calf serum (FCS) in EMEM, followed by 100 $\mu$l of a well-mixed suspension of Human WISH cells in EMEM with 5% FCA, are added to each well, to result in addition of 2.5×10$^4$ cells/well. The plates are then incubated at 37° C. in 5% CO$_2$ for 24 hours.

Approximately 24 hours after addition of the WISH cell suspension, 50 $\mu$l of VSV in EMEM, prepared in a dilution that adds at least one plaque forming unit of VSV per cell, are added to each well, with the exception of four control wells.

The virus-treated plates are incubated at 37° C. under 5% $CO_2$ and are scored approximately 18 hours after addition of the VSV.

B. Scoring

The plates are read under a light microscope, and scores recorded when the virus controls reach complete cytopathic effect (CPE) and the endpoint of the references is at the expected titer. Each test well is accorded a score as follows: SP, possible CPE; 1, 25% of cells have CPE; 2, 50% have CPE; 3, 75% of cells have CPE; 4, 100% of cells have CPE; C, bacterial contamination; and CT, cell cytotoxicity.

The endpoint of a sample titration is the well which first scores 50% CPE. The titer in $log_{10}$ units/ml of IFN corresponds to the dilution of that well, and is corrected according to the reading of the reference standard.

C. Calculation of Interferon Specific Biological Activity

The radioactivity of three 1 to 50 μl aliquots of each undiluted interferon sample is determined by counting in a Packard gamma counter. From the result in counts per minute (CPM), the counts per unit volume is determined (CPM/ml). The IFN activity (IFN units/ml) of each sample, determined according to the method described in paragraphs A and B, above, is divided by the CPM/ml value for the sample, giving the activity of the IFN in units/CPM.

The units/CPM value for each sample obtained by extraction from a manufactured polylactide system is divided by the units/CPM value for the corresponding starting stock interferon material (loading stock IFN) used to make the manufactured polylactide/interferon systems, to give the ratio of specific activity of extracted interferon to the specific activity of loading stock IFN. The ratio so obtained is multiplied by the IFN units/ml value for the loading stock IFN, which gives the loading stock IFN units/ml equivalent of the extracted IFN sample.

The $log_{10}$ of the loading stock IFN units/ml equivalent for each extracted sample is termed the relative $log_{10}$ IFN activity (RLIA). RLIA values for each group of samples tested are averaged and compared to the $log_{10}$ IFN units/ml value of the appropriate loading stock. Additional accuracy can be gained by a linear regression analysis of RLIA values obtained from a series of systems which have been implanted in a test animal, such as mice, and serially recovered at several intervals over the test period, e.g. one month. The Y-intercept of the line determined from a graph of RLIA values (Y axis) versus days of implantation (X axis) indicates the activity of the interferon in the manufactured systems prior to implantation.

D. Results

The novel controlled release systems claimed herein demonstrate RLIA values following manufacture, but prior to in vivo application, which are one/half, or more, of the $log_{10}$ IFN units/ml of the corresponding polypeptide loading stock.

Interferon/polylactide systems prepared as described in Examples 1 and 2, when assayed as described in this example, show essentially no loss of biological activity of the incorporated interferon; that is, the average RLIA values after manufacture but before implantation are essentially indistinguishable from the $log_{10}$ IFN units/ml of the IFN loading stock from which they were prepared.

EXAMPLE 6

Extraction of Polypeptide from a Polylactide Matrix

A. Extraction of Interferon from the Polylactide Matrix of Devices Prepared According to Examples 1 and 2

Interferon containing systems prepared as described in Examples 1 and 2 from a loading stock interferon spiked with a known concentration of [$^{125}$I]rHuIFN-$\beta_{ser17}$ were individually dissolved in acetone (up to 300 mg polylactide to 10 ml of acetone), and vortexed at high speed until the polylactide was completely dissolved, and the interferon left as a precipitate suspension. Each suspension was centrifuged at 700× g for 10 minutes and the acetone/polylactide supernatant removed. The residual pellet was dried for 24 hours under vacuum at room temperature, and was subsequently extracted for 1 hour with 0.5 ml of 12.5 mg/ml HSA and 12.5 mg/ml dextrose at room temperature with periodic mild agitation. Each tube was centrifuged at 700× g for 10 minutes, and the interferon-containing supernatant removed and stored at 4° C. Ten, 50 and 100 microliter samples of the supernatant were used to determine the radioactivity per unit volume. Following determination of interferon activity, the specific activity (IFN units/radioactivity counts per minute) of the extracted interferon was compared to that of the interferon stock starting material. Determination of the radioactivity per unit volume and the biological activity of the extracted interferon are described in Example 5.

EXAMPLE 7

Biological Activity of HuIFN-$\beta$ in Polylactide Delivery Devices Prepared by a Known Heat-Formation Method A. Preparation of Heat-Formed Polylactide Devices Polylactide matrix drug delivery devices containing HuIFN-$\beta$ as the active ingredient were prepared according to a known heat-extrusion method outside of the scope and practice of this invention, whereby the polypeptide and polylactide are combined and mixed in a heat extrusion apparatus. Ten grams of D,L-PLGA, (molar ratio 50/50, intrinsic viscosity 0.64 dl/gm), was mixed with the contents of 25 vials of lyophilized human recombinant interferon containing 0.3 mg IFN-$\beta$ with $4.2 \times 10^7$ interferon units, 12.5 mg human serum albumin and 12.5 mg dextrose per vial. The mixture was placed in the loading funnel of a heated extrusion device and extruded at a temperature of approximately 75° C. through a 3 mm cirucular exit die, and immediately reduced to room temperature by forced air cooling. The resulting rod of interferon/polyactide material was segmented into 7 mm lengths.

B. Extraction of Interferon

The interferon/polylactide devices formed by the method described in paragraph A were individually weighed and placed in separate 2 ml glass vials containing 1 ml of buffer solution (74.9% phosphate buffer pH 7.4, 25% ethanol and 0.1% SDS). The vials were maintained at 4° C. with mild circular agitation for 24 hours. Following extraction, the devices were removed from the vial and the extract stored at 4° C. until they were assayed.

C. Assay for Interferon Biological Activity

The interferon activity, units/ml of extract, was determined by the assay method described in Example 5. The estimated total interferon units contained in each device was calculated from the product of the dry device weight and the interferon units/gram dry weight of the formulation.

D. Results

The interferon extracted from the heat-formed devices gave an RLIA value (relative $\log_{10}$ interferon activity) of less than 1% of the $\log_{10}$ units/ml of the corresponding interferon loading stock.

EXAMPLE 8

Preparation of a Finely Divided Injectable or Implantable Controlled Release System A micro-suspension of interferon in a polylactide solution is prepared as described in Example 1 or 2. The solution is then atomized with a spray device, and the resulting particles dried and prilled as they settle in a counter-current or vortex of clean air, nitrogen, or other inert gas. The resulting particles of polypeptide/polylactide matrix are stored under vacuum for 3 days, and then sized for use or storage.

Controlled release systems prepared in this manner may be incorporated in an injectable suspension and administered subcutaneously or intramuscularly.

EXAMPLE 9

The following describes a formulation for parenteral injection of finely divided polypeptide/polylactide particles prepared according to the methods disclosed herein.

Finely divided interferon containing polylactide particles prepared as described in Example 8 are suspended in the following solution:

| | |
|---|---|
| sodium carboxymethylcellulose | 0.5% |
| NaCl | 0.6% |
| Benzyl alcohol | 0.9% |
| Tween 80 | 0.1% |
| Purified water q.s. | 100% |

For example, 330 mg of interferon/polylactide particles are suspended in 5.5 ml of the above solution to provide an injectable dose of 9 $\mu$g of interferon per 0.5 ml of injectable suspension.

The foregoing discussion and specific embodiments are intended to be exemplary of the scope and practice of this invention, and should not be read to limit the practice of the described invention.

What is claimed is:

1. A composition for the controlled administration of a biologically active macromolecular polypeptide comprising (a) a polylactide matrix in which is incorporated a micro-suspension of not more than about 30 percent by weight based on weight of the system of (b) particles of at least one biologically active macromolecular polypeptide having a molecular weight not less than about 1000 daltons, wherein substantially all of the particles of polypeptide have a diameter of 10$\mu$ or less and are uniformly and discreetly dispersed throughout the matrix, and wherein the polypeptide retains at least about 50 percent of the biological activity which it possessed prior to manufacture of the composition.

2. The system of claim 1 in which the polypeptide and other water soluble components comprise about 20 percent by weight, or less, of the matrix.

3. The system of claim 1 in which the polypeptide has a molecular weight greater than about 2,500.

4. The system of claim 3 in which the polypeptide has a molecular weight greater than about 6,000.

5. The system of claim 4 in which the polypeptide has a molecular weight greater than about 10,000.

6. The system of claim 5 in which the polypeptide is selected from the group consisting of cytokines, lymphokines, monokines and interferons.

7. The system of claim 6 in which the polypeptide is interleukin-2 or an analog thereof.

8. The system of claim 6 in which the polypeptide is an interferon.

9. The system of claim 8 which includes a pharmaceutically acceptable stabilizer for the interferon.

10. The system of claim 9 in which the interferon is a beta interferon.

11. The system of claim 10 in which the beta interferon and other water-soluble components comprise about 20 percent by weight, or less, of the matrix.

12. The system of claim 11 in which the beta interferon and other water-soluble components comprise about 10 percent by weight, or less, of the matrix.

13. The system of claim 12 in which the beta interferon and other water-soluble components comprise about 5 percent by weight, or less, of the matrix.

14. The system of claim 13 in which the stabilizer comprises either or both of human serum albumin and dextrose.

15. The system of claim 1 in which the polylactide is a poly(lactide-co-glycolide) copolymer having a molar ratio of lactide to glycolide units of between about 100:0 and 30:70.

16. The system of claim 15 in which the copolymer has a molar ratio of lactide to glycolide units of between 75:25 and 40:60.

17. The system of claim 16 in which the copolymer has a molar ratio of lactide to glycolide units of about 50:50.

18. The system of claim 17 in which the polypeptide is a recombinant human beta interferon, and in which the beta interferon and other water soluble components comprise 10 percent by weight, or less, of the matrix.

19. The system of claim 18 in which the beta interferon and other water soluble components comprise 5 percent by weight, or less, of the matrix.

20. The system of claim 1 which is formed from one or more layers of a spray-cast film.

21. The system of claim 20 which incorporates a biocompatible inert reinforcement material.

22. The system of claim 1 which contains more than one species of biologically active macromolecular polypeptide.

23. The system of claim 1 in which the polypeptide is a hormone.

24. The system of claim 23 in which the hormone is calcitonin or an analog thereof.

25. The system of claim 23 in which the hormone is parathyroid hormone or an analog thereof.

26. The system of claim 23 in which the hormone is epidermal growth factor or an analog thereof.

27. The system of claim 1 in which the polypeptide is an immunomodulator.

28. The system of claim 27 in which the polypeptide is an immune stimulator.

29. The system of claim 27 in which the polypeptide is an immune depressant.

30. The system of claim 1 in which the polypeptide is an enzyme.

31. The system of claim 30 in which the enzyme is superoxide dismutase.

32. The system of claim 30 in which the enzyme is a plasminogen activator.

33. The system of claim 32 in which the enzyme is tissue plasminogen activator.

34. The system of claim 1 in which the polypeptide is a growth promotant or growth inhibitory factor.

35. The system of claim 34 in which the polypeptide is transforming growth factor-$\beta$.

36. The system of claim 34 in which the polypeptide is a growth hormone or growth hormone releasing factor.

37. The system of claim 36 in which the polypeptide is bovine growth hormone.

38. The system of claim 1 in which the polypeptide is a blood coagulation factor.

39. The system of claim 1 in which the polypeptide is a vaccine antigen.

40. The system of claim 1 in which the polypeptide is an antibody.

41. The system of claim 1 in which the polypeptide is a protease inhibitor.

42. A composition according to claim 1 further comprising one or more other water soluble, pharmaceutically acceptable components, particles of which have a diameter of about 10$\mu$ or less, selected from the group consisting of other active agents, proteins, other polypeptides, stabilizers, carbohydrates, surfactants and plasticizers, wherein the macromolecular agent and other water soluble components together comprise about 30 percent by weight of the system.

* * * * *